US006158427A

United States Patent [19]

McGuire et al.

[11] Patent Number: 6,158,427

[45] Date of Patent: Dec. 12, 2000

[54] THERMAL CELL HAVING AN OXYGEN PERMEABLE TOP SHEET AND A METHOD OF MAKING A GAS PERMEABLE MATERIAL

[75] Inventors: Kenneth S. McGuire, Wyoming; Peter W. Hamilton, Cincinnati, both of Ohio

[73] Assignee: The Procter & Gamble Company, Cincinnati, Ohio

[21] Appl. No.: 09/281,372

[22] Filed: Mar. 30, 1999

Related U.S. Application Data

[62] Division of application No. 08/896,814, Jul. 18, 1997.

[51] Int. Cl.[7] .......... E24J 1/00

[52] U.S. Cl. .......... 126/263.01; 607/114

[58] Field of Search .......... 126/263.02, 263.05, 126/263.01, 204; 607/114, 108, 109, 110, 111, 112

[56] References Cited

U.S. PATENT DOCUMENTS

| | | | |
|---|---|---|---|
| 3,667,422 | 6/1972 | Saladin | 118/34 |
| 3,976,049 | 8/1976 | Yamashita et al. | 126/263.01 |
| 4,076,881 | 2/1978 | Sato | 428/195 |
| 4,148,958 | 4/1979 | Tischeer et al. | 428/196 |
| 4,230,463 | 10/1980 | Henis et al. | 55/16 |
| 4,243,701 | 1/1981 | Riley et al. | 427/244 |
| 4,264,659 | 4/1981 | Pattenden | 428/35 |
| 4,291,082 | 9/1981 | Stall | 428/138 |
| 4,410,568 | 10/1983 | Iwama et al. | 427/244 |
| 4,455,187 | 6/1984 | Von Blucher et al. | 156/277 |
| 4,510,193 | 4/1985 | Blucher et al. | 428/196 |
| 4,571,351 | 2/1986 | Schaetti | 427/288 |
| 4,590,098 | 5/1986 | Kazuse et al. | 427/244 |
| 4,666,644 | 5/1987 | Watson | 264/41 |
| 4,756,299 | 7/1988 | Podella | 126/263.01 |
| 4,881,954 | 11/1989 | Bikson et al. | 55/16 |
| 5,046,479 | 9/1991 | Usui | 126/204 |
| 5,051,259 | 9/1991 | Olsen et al. | 424/443 |
| 5,102,552 | 4/1992 | Callahan et al. | 210/654 |
| 5,578,344 | 11/1996 | Ahr et al. . | |
| 5,837,005 | 11/1998 | Viltro et al. | 607/112 |
| 5,918,590 | 7/1999 | Burkett et al. | 126/263.02 |
| 5,984,995 | 11/1999 | White | 126/263.05 |

FOREIGN PATENT DOCUMENTS

| | | |
|---|---|---|
| 692568 A1 | 7/1995 | European Pat. Off. . |
| 678618 A1 | 10/1995 | European Pat. Off. . |
| 708055 | 4/1954 | United Kingdom . |
| WO84/01526 | 4/1984 | WIPO . |

*Primary Examiner*—Carl D. Price
*Assistant Examiner*—David Lee
*Attorney, Agent, or Firm*—Ronald Kock; Jack L. Oney, Jr.; Loy M. White

[57] ABSTRACT

A method of making a gas permeable material having a diffusive gas permeability at 0.21 atmosphere diffusive driving force in the range of about $0.5\times10^5$ $cm^3$/100 square inches/day to about $2\times10^5$ $cm^3$/100 square inches/day. The method comprises the step of coating a pattern of spots of a gas impermeable material onto a porous substrate, followed by a step of enlarging the pattern of spots to cover greater than about 95% of the porous substrate such that the gas permeability occurs only through openings between the pattern of spots. The gas impermeable material is preferably a hot melt adhesive and the porous substrate is preferably a nonwoven. The step of enlarging the pattern of spots includes smearing substantially circular spots into oblong spots as the pattern of spots is printed onto the porous substrate until the oblong spots partially overlap. The smearing is achieved by operating a printing screen at a surface speed higher than a draw rate of the porous substrate. Alternatively, the step of enlarging the pattern of spots includes calendering through a fixed gap the porous substrate after the pattern of spots is coated thereon.

3 Claims, 4 Drawing Sheets

10
16
18
14
20
12

THERMAL CELL HAVING AN OXYGEN PERMEABLE TOP SHEET AND A METHOD OF MAKING A GAS PERMEABLE MATERIAL

CROSS-REFERENCE TO RELATED APPLICATION

This application is a divisional of U.S. application Ser. No. 08/896,814, filed Jul. 18, 1997, the disclosure of which is hereby incorporated by reference.

FIELD OF THE INVENTION

The present invention relates to methods of making a gas permeable material, and more particularly to a method wherein an impermeable material is applied to a permeable substrate and manipulated to vary the permeable area. Even more particularly, the present invention relates to such methods wherein hot melt adhesive is coated onto a nonwoven web and spread to limit oxygen permeable area to about 1% of the nonwoven area for controlling oxygen flux into a heat generating thermal cell.

BACKGROUND OF THE INVENTION

Thermal cells for body warmers are well known in the art, particularly those which use a reactive iron powder and activated carbon mixture. Such cells require oxygen to produce a controlled exothermic reaction which provides heat over several hours. Typically, the mixture is packaged in an air permeable pocket, which is sealed in an impermeable outer pouch until ready for use. The permeable pocket may be a nonwoven material. It is difficult to provide in a nonwoven material a diffusive oxygen permeability at 0.21 atmosphere driving force ranging from about $0.5\times10^5$ cubic centimeters/100 square inches/day to about quadruple that permeability. It is difficult because greater than about 95% but less than 100% of the nonwoven's surface must be occluded with an impermeable material in order to do so. This is a permeability range that others have avoided. Liquid and air filtration processes require much higher permeability ranges (typically about 50% open area), and gas separation membranes have lower permeability ranges (zero percent open area).

Gas permeable membranes have been available for separation processes. For example, U.S. Pat. No. 5,102,552 to Callahan et al., issued Apr. 7, 1992, discloses a UV curable polymer coated onto a microporous support having an average pore size from about 0.005 microns to about 0.2 microns. U.S. Pat. No. 3,754,375 to Bouchilloux et al., issued Aug. 28, 1973, discloses an "anisotropic membrane having excellent mechanical properties combined with good permeation characteristics. It comprises a vinyltriorganosilane polymer or copolymer" having a dense layer of 0.01 to 10 micron average thickness and a porous layer 20% to 80% open area.

Others have even applied gas permeable membranes to heat cells, but with limited success. For example, U.S. Pat. No. 5,046,479 to Usui issued Sep. 10, 1991, discloses a method of controlling oxygen permeation through a microporous film which is subject to a "heat fusion treatment" intended to restrict oxygen permeability to a disposable body warmer. A flat bag containing iron powder heat generating agent has an air permeable surface having an air permeability per unit of 5000 to 10,000 sec/100 cc. Such microporous films, unfortunately, are very expensive.

Others have poked small holes in an impermeable film with needles to provide oxygen permeation for heat cells in the desired range. This process is practically limited to a hole pattern wherein holes are relatively few and large. Because of this limitation, heat cell size is necessarily large. Large thermal cells have the disadvantage of being inflexible to bending to the contours of the body surface to which they are applied. Smaller "pores" created by a process that generates a finer pattern having the same permeability enables many smaller cells to be formed having greater surface conformability. Also, smaller holes are better at preventing granular thermal cell chemistry from falling out. In processing a film to provide permeability with needles, slight changes to permeability cannot easily be made. Also, film tension in the process tends to tear or otherwise enlarge holes when needle piercing occurs; thus, hole size may not be easily controlled when web tension varies.

Others have smeared adhesive onto porous webs. An example is U.S. Pat. No. 5,558,344 issued Nov. 26, 1996 to Ahr et al., which teaches the use of a printing roll having peripheral cells to apply a resinous material to a substrate web. The printing roll has at least 100% greater surface speed than that of the substrate web. The wiping process created by the surface speed differential causes the resinous material to penetrate into the substrate to cause the substrate to become water impermeable. No attempt is made by Ahr et al. to provide less than 100% coverage and there is no suggestion of using such a process for accurately controlling oxygen permeability of the substrate within a narrow range.

It is an object of the present invention to provide an inexpensive method of making an oxygen permeable material, which has a permeability in the narrow range needed for controlling heat generated within thermal cells.

It is a further object of the present invention to provide a method for making a gas permeable material, which is directly sealable to the flange of an impermeable pocket containing a thermal mixture without the need for heat sealing.

It is yet another object to provide a method for making a gas permeable material wherein a simple process change can be made to slightly vary the oxygen permeation of the material within a desired narrow range.

SUMMARY OF THE INVENTION

In one aspect of the present invention, a method of making a diffusive gas permeable material having a gas permeability at 0.21 atmosphere driving force in the range of about $0.5\times10^5$ $cm^3$/100 square inches/day to about $2\times10^5$ $cm^3$/100 square inches/day, comprises the steps of first coating a pattern of spots of a gas impermeable material onto a porous substrate, and then enlarging the pattern of spots to cover greater than about 95%, and preferably about 99%, of the porous substrate such that the diffusive gas permeability occurs only through openings between the pattern of spots. Preferably the diffusive gas permeability is diffusive oxygen permeability, but it may also include carbon dioxide or other gases. The gas impermeable material is preferably a hot melt adhesive and the porous substrate is preferably a nonwoven.

The step of enlarging the pattern of spots may comprise smearing substantially circular spots into oblong spots as the pattern of spots is printed onto the porous substrate. The substantially circular spots are preferably arranged such that the smearing causes the oblong spots to partially overlap. The smearing is achieved by operating a rotary printing screen at a surface speed higher than a draw rate of the porous substrate.

Alternatively, the step of enlarging the pattern of spots may comprise calendering through a fixed gap the porous substrate after the pattern of spots is coated thereon. The fixed gap has a dimension smaller than a thickness of the porous substrate and the pattern of spots, such that each spot of the pattern of spots is enlarged to partially overlap other spots after calendering. The pattern of spots are preferably enlarged such that an enlarged individual spot partially overlaps at least two other enlarged equidistant spots to generate substantially uniformly sized and shaped openings between all of the equidistant spots.

In another aspect of the present invention, a thermal cell comprises a bottom sheet formed to have an oxygen impermeable pocket, a plurality of particles reacting exothermally when exposed to oxygen placed in the pocket, and a top sheet sealed to the bottom sheet at a flange of the pocket to enclose the plurality of particles such that the particles cannot exit the pocket. The top sheet has a porous substrate, which is coated with a pattern of spots made of an oxygen impermeable material. The oxygen impermeable material uniformly covers greater than about 95% of a surface of the porous substrate such that the top sheet has a diffusive gas permeability at 0.21 atmosphere driving force ranging from about $0.5\times10^5$ $cm^3$/100 square inches/day to about $2\times10^5$ $cm^3$/100 square inches/day.

The oxygen impermeable material is preferably a hot melt adhesive and the porous substrate is preferably a nonwoven. The hot melt adhesive is preferably on a pocket-facing side of the porous substrate so that the hot melt adhesive also may serve to seal the top sheet to the bottom sheet.

BRIEF DESCRIPTION OF THE DRAWINGS

While the specification concludes with claims which particularly point out and distinctly claim the present invention, it is believed that the present invention will be better understood from the following description of preferred embodiments, taken in conjunction with the accompanying drawings, in which like reference numerals identify identical elements and wherein:

DETAILED DESCRIPTION OF THE INVENTION

Figure 1:
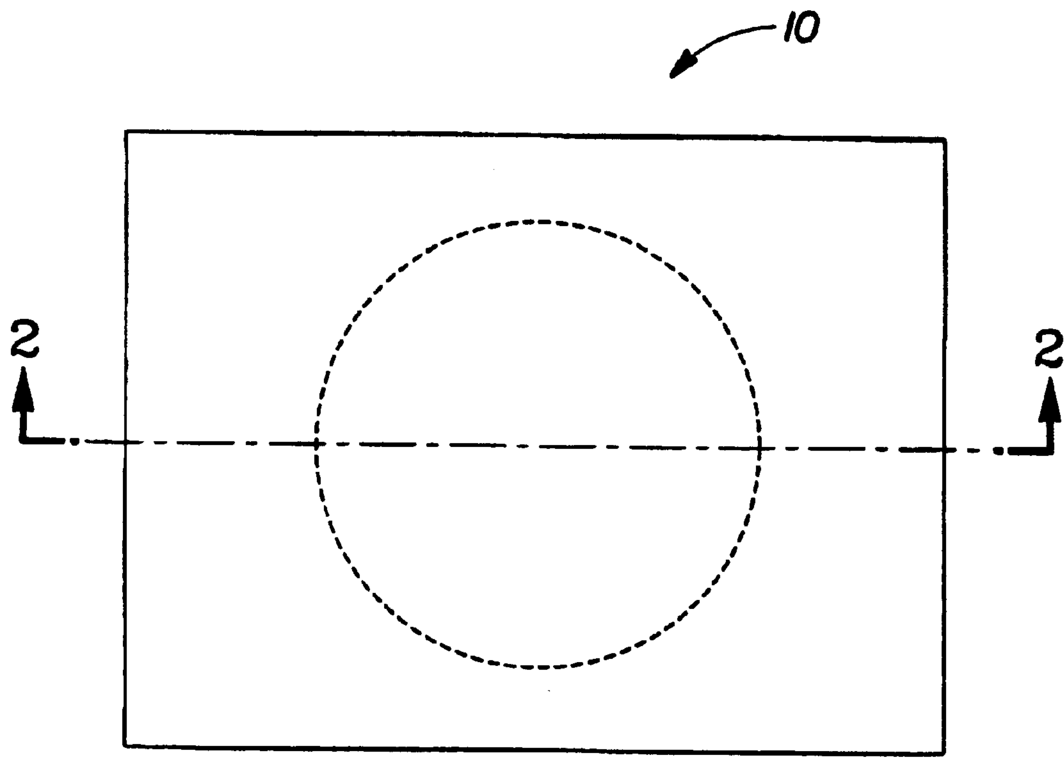
FIG. 1 is a top plan view of a preferred embodiment of a thermal cell of the present invention, disclosing a substantially circular cell covered by an oxygen permeable top sheet.
Figure 2:
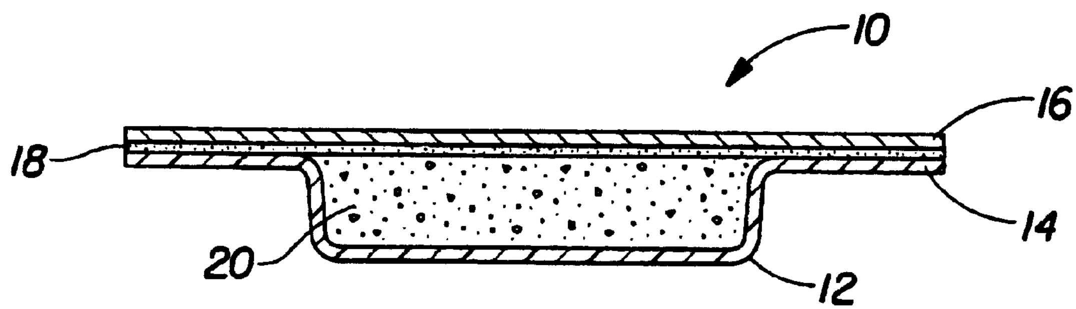
FIG. 2 is a sectioned front elevation view, taken along section line 2—2 of FIG. 1, showing a pocket formed in an oxygen impermeable bottom sheet, particles of heat generating material in the pocket, and a topsheet covering the pocket, wherein the topsheet comprises a porous substrate and a patterned layer of oxygen impermeable material between the top sheet and bottom sheet.

Referring now to the drawings, and more particularly to FIGS. 1 and 2, there is shown a first preferred embodiment of the present invention, which provides a thermal cell and is generally indicated as 10. Thermal cell 10 has a pocket 12 formed in a gas impermeable bottom sheet 14, such as 0.025 mm thick low density polyethylene film. Thermal cell 10 also has a gas permeable top sheet 16, which is preferably a nonwoven coated with an occluding material 18 to limit the diffusive gas permeability of the nonwoven. Top sheet 16 is preferably made of a 14 gram per square meter polypropylene nonwoven. Occluding material 18 is preferably a hot melt adhesive, such as CA-X-105-A3, made by Century International of Columbus, Ohio. A pressure sensitive adhesive would be more preferable because it is an ideal occluding material when it is coated on the side of top sheet 16 which faces bottom sheet 14, and the two sheets can be combined without heat sealing.

Pocket 12 is preferably circular, having a diameter of about 12.5 mm and a depth of about 6.5 mm. Inserted within pocket 12 is a heat generating chemistry 20, which is preferably particles of powdered iron, powdered activated charcoal, water and salt. Such chemistry requires oxygen to initiate an exothermic reaction. When the rate of oxygen entry to the pocket is controlled, the temperature and time of heat generation is controlled; thus, the importance of oxygen permeability to the pocket through top sheet 16. Further details concerning thermal cell 12, may be found in copending application Ser. No. 08/496,659, entitled "HEAT CELLS", filed on Jun. 29, 1995, and assigned to the assignee of the present application, which is hereby incorporated herein by reference.

The desired oxygen permeability for thermal cell 12 ranges from about $0.5\times10^5$ $cm^3$/100 square inches/day to about $2\times10^5$ $cm^3$/100 square inches/day when driven by a 0.21 atmosphere partial pressure. The 0.21 atmosphere driving force means that there is an oxygen partial pressure on one side of the substrate higher than on the other side. That is, there is no overall pressure differential, only an oxygen concentration difference from one side of the substrate to the other. With this permeability, exclusively provided by top sheet 16, heat generation may last for about 8 hours at a temperature range of about 40° C. to about 43° C.

When top sheet 16 is a nonwoven coated with hot melt adhesive 18 such that greater than about 95% of the surface of the nonwoven is occluded, particles of the heat generating chemistry are effectively held in pocket 12 without falling out when thermal cell 10 is handled.

Figure 3:
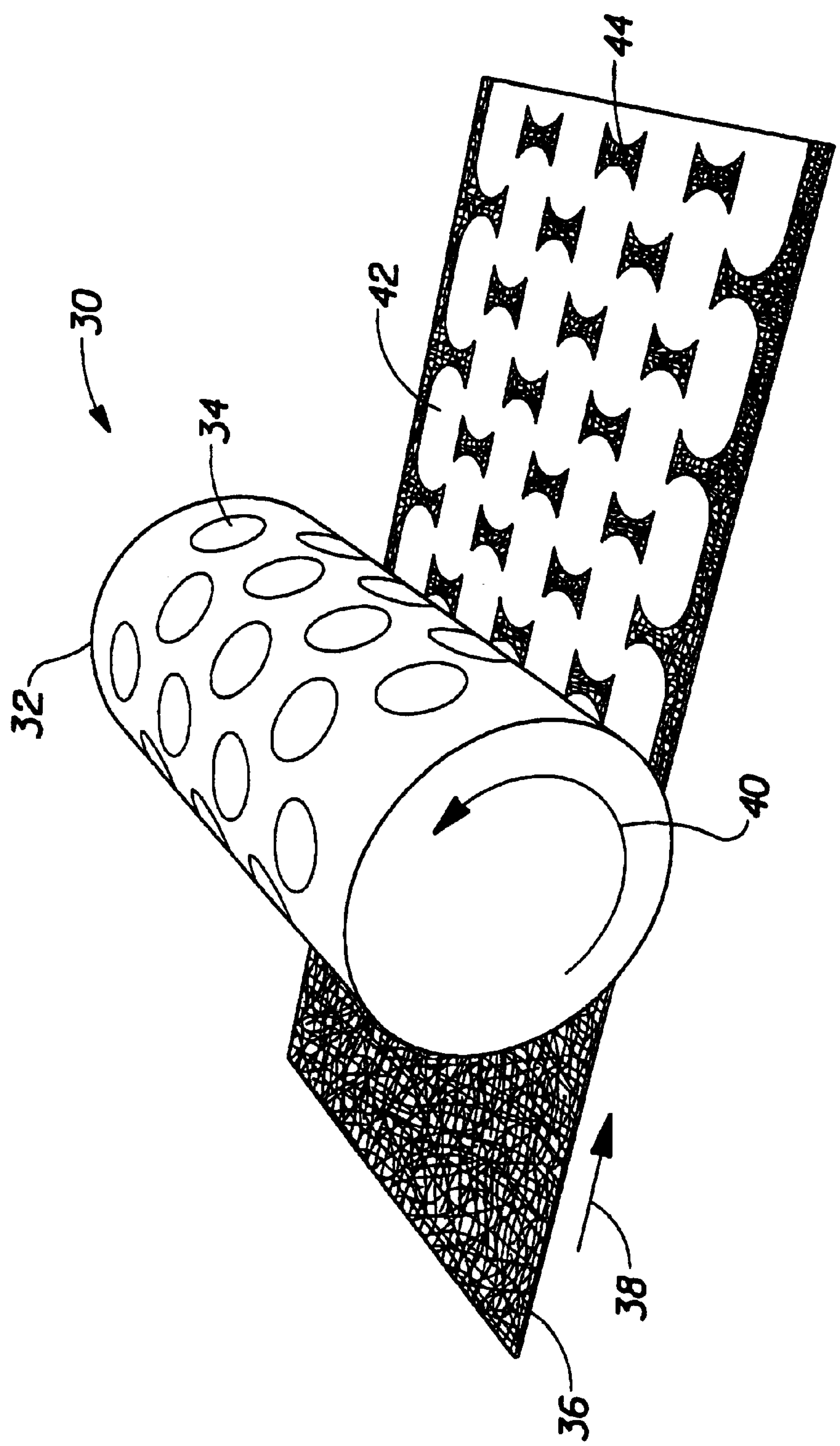
FIG. 3 is a side elevation perspective view of a method of making the top sheet of the present invention, disclosing a printing roll applying substantially circular spots of a gas impermeable material to a porous substrate at a faster surface rate than a draw rate of the substrate such that the spots are smeared to an oblong shape on the porous substrate.
Figure 4:
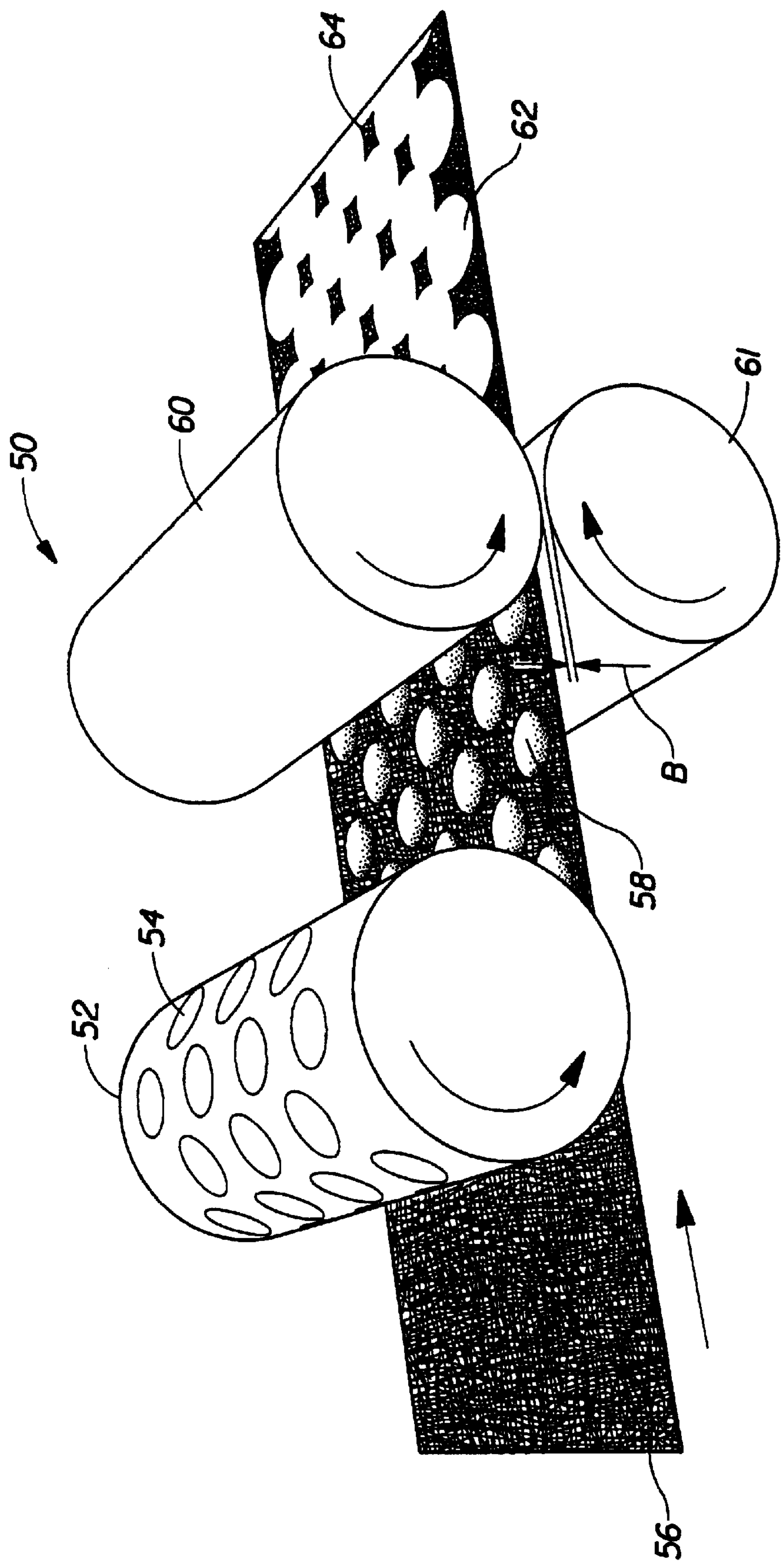
FIG. 4 is a side elevation perspective view of an alternative method of making the top sheet of the present invention, disclosing a roll coating substantially circular spots of a gas impermeable material onto a porous substrate followed by a calendering step wherein the spots are enlarged to overlap.

Preferred methods of the present invention are illustrated in FIGS. 3 and 4. FIG. 3 shows a roll coating process, generally indicated as 30, in which a roll 32 is coated with or has at its surface substantially circular spots 34 of an occluding material. A web of gas permeable top sheet material 36 is passed under roll 32 at a surface speed 38, which is less than a surface speed 40 of roll 32. When spots 34 transfer from roll 32 to web 36, the surface speed differential causes substantially circular spots 34 to be smeared longitudinally on web 36 to form oblong spots 42 of the occluding material on top sheet web 36. Preferably, spots 34 are placed on roll 32 such that when smeared on web 36, spots 42 will partially overlap except at their longitudinal ends. Between longitudinal ends of smeared spots 42 there is an opening 44, which provides access for gas to permeate top sheet web 36.

In a preferred embodiment, roll 32 is about 220 mm in diameter and has a surface speed 40 of 0.21 m/sec. Top sheet web 36 is preferably a nonwoven which has a surface speed 38 of about 0.13 m/sec, for a surface speed ratio of 1.61. Substantially circular spots 34 are preferably hot melt pressure sensitive adhesive extruded through the surface of roll 32 by a common screen printing process, not shown. The screen preferably has a #40 standard mesh and is made by Stork Screens of America, Inc. of Charlotte, N.C. At a printing temperature of about 260° F., a coat weight of about 47 grams per square meter is deposited onto top sheet web 36. After smearing spots 34 on web 36, resulting spots 42 partially overlap, and gas permeability of nonwoven top sheet web 36 preferably ranges from about $0.5\times10^5$ $cm^3$/100 square inches/day to about $2\times10^5$ $cm^3$/100 square inches/day.

Method 30 is applicable to occluding materials other than hot melt adhesive and nonwoven webs. For example, thermoplastics, thermosets, and/or high viscosity fluids can be cooled onto microporous membranes, paper, and fine screens. Also, spots 34 could be other than substantially circular. For example, they could be oval with lateral length being greater than longitudinal length. The resulting smearing could produce substantially circular spots on the web. Polygonal spots could also be transferred and smeared onto web 36 in order to shape the openings between smeared spots to any shape desired.

Figure 5:
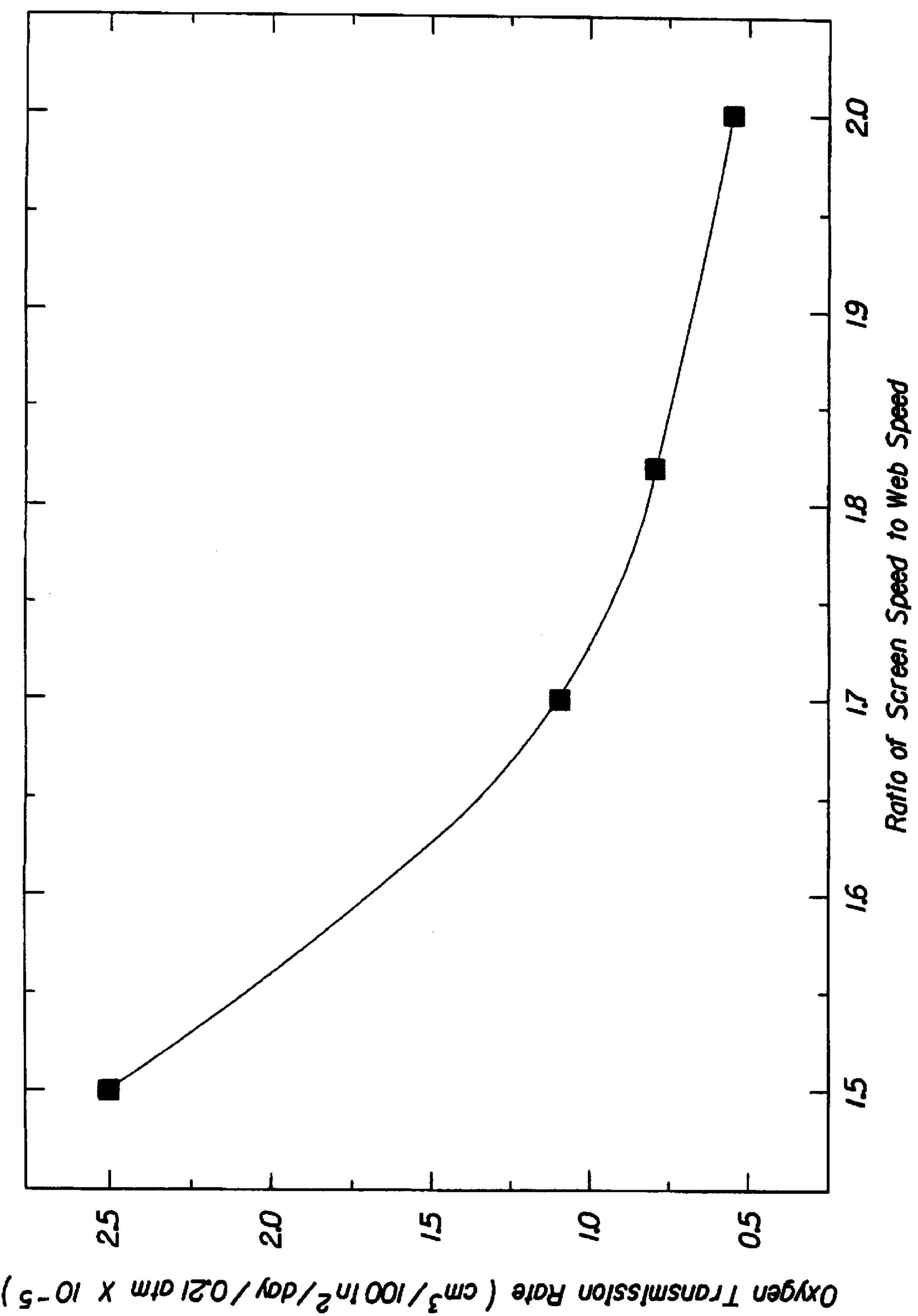
FIG. 5 is a graph of diffusive oxygen permeability versus ratio of print roll speed to porous substrate web speed for the alternative of hot melt smearing of printed spots.

FIG. 5 shows the effect on diffusive oxygen permeability through a substrate web by altering the ratio of surface speeds of the rotating screen of a screen printer and the porous substrate web to be printed. The web speed is held constant at 0.13 meters per second while the surface speed of the screen is adjusted between 0.19 and 0.26 meters per second. As can be seen from FIG. 5, as the ratio of screen speed to web speed is increased, the diffusive oxygen permeability is decreased. The diffusive oxygen permeability decrease is a result of the spots of hot melt adhesive being smeared to a greater extent and thereby occluding a greater percentage of the open area of the porous substrate.

FIG. 4 shows an alternative preferred method of the present invention, generally indicated as 50. Method 50 is a two step spot transfer and calendering process. A first roll 52 is similar to roll 32 of FIG. 3, and substantially circular spots 54 of occluding material are placed on roll 52. A web of gas permeable top sheet material 56 is passed under roll 52 and spots 54 are transferred from roll 52 to web 56 to form transferred spots 58. Method 50 includes a second roll or pair of rolls 60 and 61, which preferably have a fixed gap B between them which is smaller than the combined thickness of web 56 and spots 58. Rolls 60 and 61 therefore calender spots 58 to larger spots 62, which overlap and have substantially rectangular openings 64 between spots 62. Openings 64 provide access for gas to permeate top sheet web 56. A differential surface speed is not needed for this embodiment, but one may be present so as to partially enlarge spots 58 before they are calendered. Substantially circular spots 54 are preferably hot melt adhesive placed on a surface of roll 52 by a common screen printing process, not shown. These spots preferably do not overlap at this stage of method 50, however, some overlap is permitted. After calendering spots 58 on web 56, resulting spots 62 preferably do partially overlap, and diffusive gas perneability of calendered nonwoven top sheet web 56 preferably ranges from about $0.5\times10^5$ $cm^3$/100 square inches/day to about $2\times10^5$ $cm^3$/100 square inches/day.

Method 50 is applicable to occluding materials other than hot melt adhesive and nonwoven webs. For example, thermoplastics, thermosets, and/or high viscosity fluids can be calendered onto microporous membranes, paper, and fine screens. Also, spots 54 could be other than substantially circular. For example, they could be oval with lateral length being greater than longitudinal length. Polygonal spots could also be transferred onto web 56 in order to shape the openings between enlarged spots to any shape desired.

While particular embodiments of the present invention have been illustrated and described, it will be obvious to those skilled in the art that various changes and modifications may be made without departing from the spirit and scope of the invention, and it is intended to cover in the appended claims all such modifications that are within the scope of the invention.

What is claimed is:

1. A thermal cell comprising:

a) a bottom sheet formed to have a pocket, said bottom sheet being impermeable to oxygen;

b) a plurality of particles placed in said pocket, said plurality of particles reacting exothermally when exposed to oxygen; and c) a top sheet sealed to said bottom sheet at a flange of said pocket to enclose said plurality of particles such that said particles cannot exit said pocket, said top sheet having a porous substrate, said substrate being coated with a pattern of spots made of hot melt adhesive, said hot melt adesive uniformly covering greater than about 95%of a surface of said porous substrate such that said top sheet has a diffusive oxygen permeability at 0.21 atmosphere diffusive driving force ranging from about $0.5\times10^5 cm^3$/100 square inches/day to about $2\times10^5$ $cm^3$/100 square inches/day.

2. The thermal cell of claim 1 wherein said porous substrate is a nonwoven.

3. The thermal cell of claim 1 wherein said hot melt adhesive is on a pocket-facing side of said porous substrate so that said hot melt adhesive may also serve to seal said top sheet to said bottom sheet.

* * * * *